(12) United States Patent
Kavuru

(10) Patent No.: US 11,440,908 B2
(45) Date of Patent: Sep. 13, 2022

(54) CRYSTALLINE FORMS OF DASATINIB

(71) Applicant: Johnson Matthey Public Limited Company, London (GB)

(72) Inventor: Padmini Kavuru, Townsend, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/949,260

(22) Filed: Oct. 22, 2020

(65) Prior Publication Data

US 2021/0032235 A1    Feb. 4, 2021

Related U.S. Application Data

(63) Continuation of application No. PCT/US2019/028853, filed on Apr. 24, 2019.

(60) Provisional application No. 62/662,379, filed on Apr. 25, 2018.

(51) Int. Cl.
  *C07D 417/12*    (2006.01)

(52) U.S. Cl.
  CPC ........ *C07D 417/12* (2013.01); *C07B 2200/13* (2013.01)

(58) Field of Classification Search
  CPC .................................................. C07D 417/12
  USPC ......................................................... 544/333
  See application file for complete search history.

(56) References Cited

U.S. PATENT DOCUMENTS

| | | | |
|---|---|---|---|
| 7,491,725 B2 | 2/2009 | Lajeunesse et al. | |
| 7,973,045 B2 | 7/2011 | Simo et al. | |
| 8,067,423 B2 | 11/2011 | Simo et al. | |
| 8,242,270 B2 | 8/2012 | Lajeunesse et al. | |
| 8,680,103 B2 | 3/2014 | Lajeunesse et al. | |
| 8,884,013 B2 | 11/2014 | Yan | |
| 9,249,134 B2 | 2/2016 | Dwivedi et al. | |
| 9,340,536 B2 | 5/2016 | Chiodo et al. | |
| 9,456,992 B2 | 10/2016 | Brisander et al. | |
| 9,556,164 B2 | 1/2017 | Hafner et al. | |
| 9,884,857 B2 | 2/2018 | Hafner et al. | |
| 10,508,096 B2* | 12/2019 | Dull ...................... | A24B 15/38 |
| 2014/0031352 A1 | 1/2014 | Gorantla et al. | |
| 2016/0250153 A1 | 9/2016 | Brisander et al. | |
| 2016/0264565 A1 | 9/2016 | Rampalli et al. | |
| 2016/0361313 A1 | 12/2016 | Brisander et al. | |
| 2017/0183334 A1 | 6/2017 | Marvanyos et al. | |

FOREIGN PATENT DOCUMENTS

| | | |
|---|---|---|
| CN | 102643275 A | 8/2012 |
| CN | 103059013 A | 4/2013 |
| CN | 103819469 A | 5/2014 |
| CN | 104341410 A | 2/2015 |
| WO | 2009147238 A1 | 12/2009 |
| WO | 2010062715 A2 | 6/2010 |
| WO | 2010067374 A2 | 6/2010 |
| WO | 2010139979 A2 | 12/2010 |
| WO | 2010139980 A1 | 12/2010 |
| WO | 2010139981 A2 | 12/2010 |
| WO | 2011003853 A2 | 1/2011 |
| WO | 2011095588 A1 | 8/2011 |
| WO | 2012014149 A1 | 2/2012 |
| WO | 2013065063 A1 | 5/2013 |
| WO | 2014086326 A1 | 6/2014 |
| WO | 2015107545 A1 | 7/2015 |
| WO | 2015181573 A1 | 12/2015 |
| WO | 2016001025 A1 | 1/2016 |
| WO | 2017002131 A1 | 1/2017 |
| WO | 2017103057 A1 | 6/2017 |
| WO | 2017108605 A1 | 6/2017 |
| WO | 2017134615 A1 | 8/2017 |
| WO | 2017134617 A1 | 8/2017 |

OTHER PUBLICATIONS

Bernstein, Polymorphism in Molecular Crystals, Clarendon Press Oxford, 115-118 and 272. (Year: 2002).*
Dean "Analytical Chem . . . " p. 10.24-10.26 (1995).*
Seddon "Pseudopolymorph . . . " Crystal Growth & design v.4(6) p. 1087 (2004) (2 pages from internet).*
Ivanisevic et al., "Use of X-ray . . . "Pharm. Sci. Encycl. p. 1-42 (2010).*
Ivanisevic et al I., "Uses of X-ray, etc.," Pharm. Form. Qual. 2011, pp. 30-33.*
Bhattacharya et al., "Thermoanalytical and Crystallographic Methods" in Brittain H. ed., 2nd ed. Informa Healthcare: NY2009 p. 318-335.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Stahly, "Diversity in Single-, etc.", Crystal Growth & Design, 7 (6), 2007, 1007-1026.*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*

* cited by examiner

*Primary Examiner* — Charanjit Aulakh

(57) ABSTRACT

The present disclosure relates to a dasatinib co-crystal form comprising dasatinib and a second compound, also referred to as a co-crystal former, wherein the second compound is selected from butyl paraben, propyl paraben and ethyl vanillin. The present disclosure is also related to an ethyl formate solvate form of dasatinib. The present disclosure is also related to processes for the preparation of the dasatinib co-crystal and solvate forms of dasatinib. Further, the present disclosure also relates to pharmaceutical compositions comprising the dasatinib co-crystal and solvate forms of dasatinib and methods for treating disease using the dasatinib co-crystal and solvate forms of dasatinib.

7 Claims, 16 Drawing Sheets

CRYSTALLINE FORMS OF DASATINIB

CROSS-REFERENCE TO RELATED APPLICATIONS

This application is a continuation of International Application No. PCT/US2019/028853, filed Apr. 24, 2019, which claims priority to U.S. Provisional Patent Application No. 62/662,379, filed Apr. 25, 2018, the disclosures of which are incorporated herein by reference in their entireties for all purposes.

FIELD OF THE DISCLOSURE

The present disclosure relates to crystalline forms of dasatinib. The present disclosure relates to a multicomponent co-crystalline system comprising dasatinib and a second compound, which acts as a co-crystal former (dasatinib co-crystal). The present disclosure is also related to a solvate form of dasatinib. Further, the present disclosure is also related to processes for the preparation of the dasatinib co-crystal and solvated forms. Further, the present disclosure also relates to pharmaceutical compositions comprising the dasatinib co-crystal and solvated forms, and methods for treating disease using the forms.

BACKGROUND OF THE DISCLOSURE

Dasatinib (DAS), having the chemical designation N-(2-chloro-6-methylphenyl)-2-[[6-[4-(2-hydroxyethyl)-1-piperazinyl]-2-methyl-4-pyrimidinyl]amino]-5-thiazolecarboxamide, monohydrate, is an orally bioavailable inhibitor of the receptor tyrosine kinase (RTK) epidermal growth factor receptor (ErbB; EGFR) family, with antineoplastic activity. Dasatinib has the following structure:

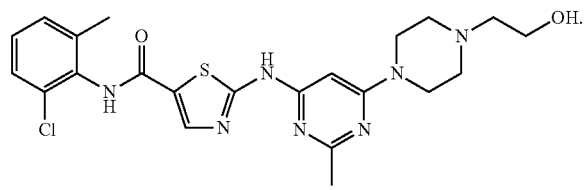 [SMILES: Cc1nc(Nc2ncc(C(=O)Nc3c(C)cccc3Cl)s2)cc(N2CCN(CCO)CC2)n1]

Dasatinib is commercially marketed under the name SPRYCEL® and is indicated for the treatment of patients with newly diagnosed Philadelphia chromosome-positive chronic myeloid leukemia in chronic phase, for the treatment of patients chronic, accelerated, or myeloid or lymphoid blast phase Philadelphia chromosome-positive chronic myeloid leukemia with resistance or intolerance to prior therapy and for the treatment of patients with Philadelphia chromosome-positive acute lymphoblastic leukemia with resistance or intolerance to prior therapy.

Solid forms of dasatinib are described in U.S. Pat. No. 7,491,725 (butanol solvate, monohydrate, diethanolate, hemi-ethanolate, anhydrous), U.S. Pat. No. 8,680,103 (butanol solvate, monohydrate, diethanolate, hemi-ethanolate, anhydrous), U.S. Pat. No. 7,973,045 (anhydrous), U.S. Pat. No. 8,067,423 (isopropyl alcohol solvate), U.S. Pat. No. 8,242,270 (butanol solvate, monohydrate, diethanolate, hemi-ethanolate, anhydrous), U.S. Pat. No. 8,884,013 (monohydrates), U.S. Pat. No. 9,249,134 (amorphous), U.S. Pat. No. 9,456,992 (solid dispersion nanoparticles), U.S. Pat. No. 9,556,164 (saccharin salt crystal) and U.S. Pat. No. 9,884,857 (saccharinate, glutarate, nicotinate); in U.S. Publication Nos. 20160250153 (solid dispersion nanoparticles), 20160264565 (Form-SDI), 20160361313 (solid dispersion nanoparticles), 20170183334 (salts) and 20140031352 (antioxidative acid); in International Publication Nos. WO2010067374 (solvated forms and Form I), WO2010139980, WO2010139981, WO2013065063 (anhydrous), WO2017103057, WO2017108605 (solid dispersion), WO2017134617 (amorphous), WO2014086326 (NMP, isoamyl-OH, 1,3-propanediol process), WO2015107545, WO2015181573, WO2017134615 (PG solvate), WO2010062715 (isosorbide dimethyl ether, N,N'-dimethylethylene urea, N,N'-dimethyl-N,N'-propylene urea), WO2010139979 (DCM, DMSP, monohydrate), WO2011095588 (anhydrate, hydrochloride, hemi-ethanol), WO2012014149 (N-methylformamide) and WO2017002131 (propandiol, monohydrate); and in Chinese Patent Nos. CN102643275, CN103059013, CN103819469, CN104341410. None of the references describe an ethyl formate solvate of dasatinib.

Dasatinib co-crystals are described in U.S. Pat. No. 9,340,536 (co-crystals selected from methyl-4-hydroxybenzoate, nicotinamide, ethyl gallate, methyl gallate, propyl gallate, ethyl maltol, vanillin, menthol, and (1R,2S,5R)-(−)-menthol) and International Publication No. WO2016001025 (co-crystal selected from menthol or vanillin). None of the references describe dasatinib co-crystal comprising dasatinib and a second compound, as a co-crystal former, wherein the second compound is selected from butyl paraben, propyl paraben and ethyl vanillin.

SUMMARY OF THE DISCLOSURE

The present disclosure relates to a dasatinib co-crystal form comprising dasatinib and a second compound ($2^{nd}$ compound), also referred to as a co-crystal former, wherein the second compound is selected from butyl paraben, propyl paraben and ethyl vanillin. The present disclosure is also related to an ethyl formate solvate form of dasatinib. The present disclosure is also related to processes for the preparation of the dasatinib co-crystal and solvate forms of dasatinib. Further, the present disclosure also relates to pharmaceutical compositions comprising the dasatinib co-crystal and solvate forms of dasatinib and methods for treating disease using the dasatinib co-crystal and solvate forms of dasatinib.

DETAILED DESCRIPTION OF THE DISCLOSURE

Figure 1:
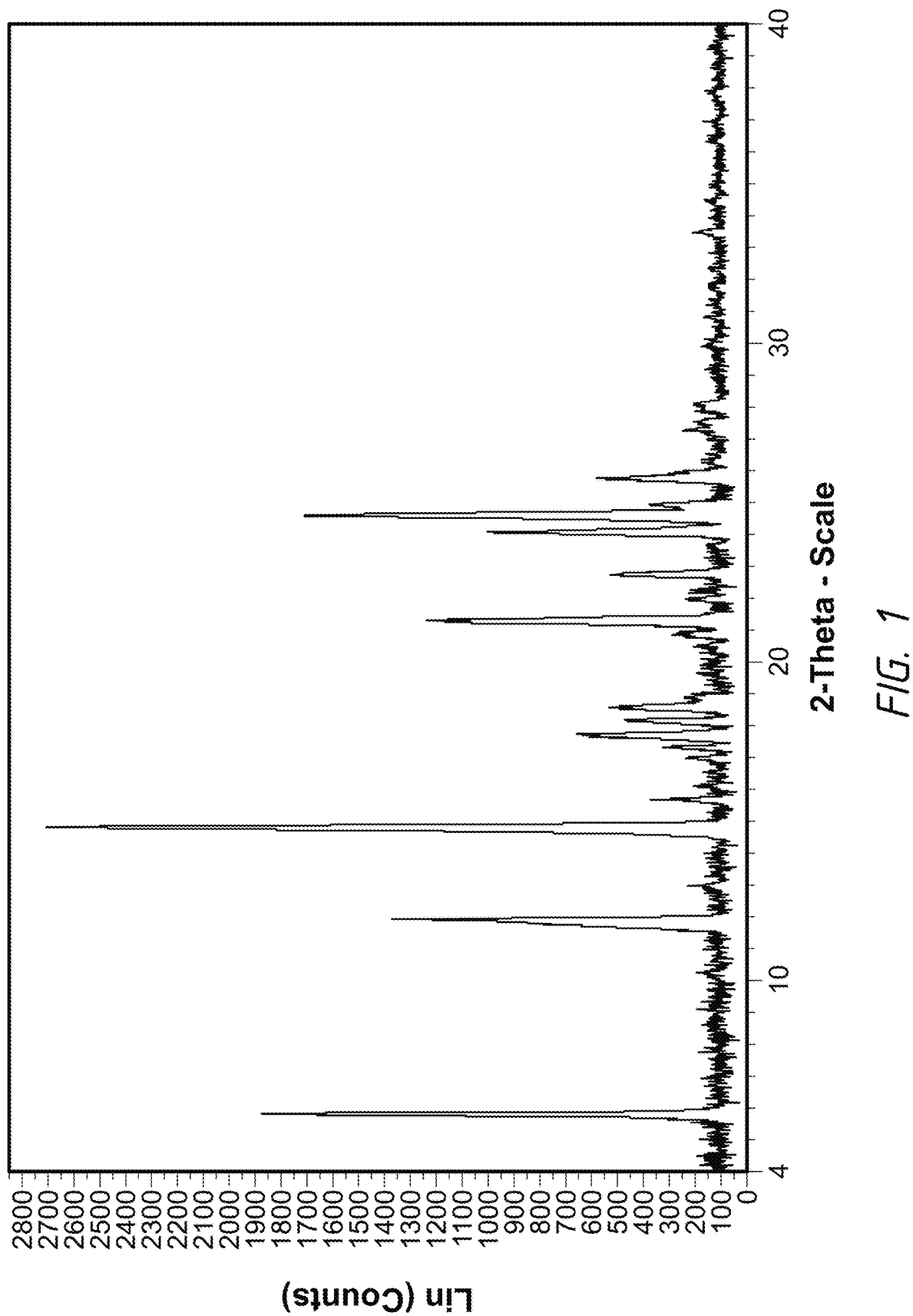
FIG. 1 is an XRPD pattern of Form I of ethyl formate solvate of dasatinib.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are not intended to be limited to the examples described herein and shown, but are to be accorded the scope consistent with the claims.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form.

As used herein and unless otherwise specified, "co-crystal" and "multicomponent crystalline systems" refer to solid materials composed of two or more different molecular and/or ionic compounds in a stoichiometric ratio which interact through non-covalent interactions which can be designed utilizing supramolecular synthon approach. The co-crystal in which at least one of the components is dasatinib and the other is a second pharmaceutically acceptable compound, is called a pharmaceutical dasatinib co-crystal.

As used herein and unless otherwise specified, the term "pharmaceutical composition" is intended to encompass a pharmaceutically effective amount of the dasatinib co-crystal and solvate forms of dasatinib of the invention and a pharmaceutically acceptable excipient. As used herein, the term "pharmaceutical compositions" includes pharmaceutical compositions such as tablets, pills, powders, liquids, suspensions, emulsions, granules, capsules, suppositories, or injection preparations.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "excipient" refers to a pharmaceutically acceptable organic or inorganic carrier substance. Excipients may be natural or synthetic substances formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

As used herein and unless otherwise specified, the term "patient" refers to an animal, preferably a mammal, most preferably a human, who has been the object of treatment, observation or experiment. Preferably, the patient has experienced and/or exhibited at least one symptom of the disease or disorder to be treated and/or prevented. Further, a patient may not have exhibited any symptoms of the disorder, disease or condition to be treated and/or prevented, but has been deemed by a physician, clinician or other medical professional to be at risk for developing said disorder, disease or condition.

As used herein and unless otherwise specified, the terms "polymorph," "polymorphic form" or related term herein, refer to a crystal form of one or more molecules, or solvate or salt thereof that can exist in two or more forms, as a result different arrangements or conformations of the molecule(s), or solvate molecule or salt ion thereof in the crystal lattice of the polymorph.

As used herein and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more therapeutic agents to a patient with such a disease or disorder. In some embodiments, the terms refer to the administration of a compound provided herein, with or without other additional active agents, after the onset of symptoms of a disease.

The present disclosure relates to a dasatinib co-crystal comprising dasatinib and a second compound, also referred to as a co-crystal former, wherein the second compound is selected from butyl paraben, propyl paraben and ethyl vanillin. The present disclosure is also related to an ethyl formate solvate form of dasatinib. The present disclosure is also related to processes for the preparation of the dasatinib co-crystal and solvate forms of dasatinib. Further, the present disclosure also relates to pharmaceutical compositions comprising the dasatinib co-crystal and solvate forms of dasatinib and methods for treating disease using the dasatinib co-crystal and solvate forms of dasatinib.

A further embodiment of the invention is wherein the dasatinib and second compound are in molar ratio of 1:1.

In another embodiment, the dasatinib co-crystal comprises dasatinib and butyl paraben. The aforesaid embodiment wherein the dasatinib and butyl paraben are in molar ratio of 1:1.

In another embodiment, the dasatinib co-crystal comprises dasatinib and ethyl vanillin. The aforesaid embodiment wherein the dasatinib and ethyl vanillin are in molar ratio of 1:1

In another embodiment, the dasatinib co-crystal comprises dasatinib and propyl paraben. The aforesaid embodiment wherein the dasatinib and propyl paraben are in molar ratio of 1:1.

Another embodiment according to the invention is wherein the ethyl formate solvate form of dasatinib is useful for the preparation of the dasatinib co-crystal comprised of dasatinib and ethyl vanillin.

Another embodiment according to the invention is wherein the dasatinib co-crystal comprised of dasatinib and ethyl vanillin is prepared from an ethyl formate solvate form of dasatinib.

Another embodiment according to the invention is a method of making the dasatinib co-crystal, comprising dissolving dasatinib and a second compound, wherein the second compound is selected from the group consisting of butyl paraben, propyl paraben and ethyl vanillin, in heated methanol (~10:1-wt$(mg)_{DAS}$:v$(mL)_{MeOH}$ and mol$_{DAS}$:mol$_{2nd\ compound}$ is 1:1.1) to form a clear solution, heating the solution under vacuum for about 18-20 h to yield the dasatinib co-crystal.

A further embodiment according to the invention is a method for the preparation of Form II co-crystal of dasatinib and ethyl vanillin comprising:
 (a) dissolving Form I of ethyl formate solvate of dasatinib and ethyl vanillin in N-methyl-2-pyrrolidone to form a solution;
 (b) adding water to the solution;
 (c) stirring the solution for about 12-24 hours to form a slurry;
 (d) filtering the slurry to yield a precipitate;
 (e) washing the precipitate with water; and
 (f) drying the precipitate under vacuum with warming to yield Form II co-crystal of dasatinib and ethyl vanillin.

Yet a further embodiment according to the invention is a method for the preparation of Form I of ethyl formate solvate of dasatinib, comprising:
 (a) dissolving dasatinib in ethyl formate to form a solution;
 (b) stirring the solution for about 12-24 hours to form a slurry;
 (c) filtering the slurry to yield Form I of ethyl formate solvate of dasatinib.

Yet a further embodiment according to the invention is a method for the preparation of Form I of ethyl formate solvate of dasatinib, comprising:
 (a) dissolving dasatinib in N-Methyl-2-pyrrolidone to form a solution;
 (b) adding ethyl formate to the solution to form a slurry;
 (c) adding additional ethyl formate to the slurry;
 (d) stirring the slurry for about 2 hours;
 (e) filtering the slurry to yield a precipitate; and
 (f) washing the precipitate with ethyl formate to yield Form I of ethyl formate solvate of dasatinib.

The present disclosure provides for a method of treating disease by administering to a patient, in need thereof, a pharmaceutical composition comprising the dasatinib co-crystal form according to the invention. Dasatinib is indicated for adults with newly diagnosed Philadelphia chromosome-positive (Ph+) chronic myeloid leukemia (CML) in chronic phase, adults with Ph+ CML who no longer benefit from, or did not tolerate, other treatment; adults with Ph+ acute lymphoblastic leukemia (Ph+ ALL) who no longer benefit from, or did not tolerate, other treatment; and children with Ph+ CML in chronic phase.

The present disclosure also encompasses pharmaceutical compositions comprising the dasatinib co-crystal and solvated forms according to the invention. Pharmaceutical compositions containing the dasatinib co-crystal and solvated forms according to the invention may be prepared according to International Publication Nos. WO2009/147238 and WO2011/003853, which are incorporated herein by reference in their entireties. The dosage of the pharmaceutical compositions may be varied over a wide range. Optimal dosages and dosage regimens to be administered may be readily determined by those skilled in the art, and will vary with the mode of administration, the strength of the preparation and the advancement of the disease condition. In addition, factors associated with the patient being treated, including patient's sex, age, weight, diet, physical activity, time of administration and concomitant diseases, will result in the need to adjust dosages and/or regimens. For example, a dosage of the pharmaceutical composition of the invention is available as tablets in amounts of 20 mg, 50 mg, 70 mg, 80 mg, 100 mg or 140 mg. The recommended dose of dasatinib is 100 mg, orally, once daily for chronic phase CML in adults and 140 mg, orally, once daily for accelerated phase CML, myeloid or lymphoid blast phase CML, or Ph+ ALL in adults. The recommended starting dose is based on body weight for pediatric patients with chronic phase CML.

EXAMPLES

Examples, which follow herein, are directed to embodiments of the invention. The examples are presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present disclosure and the disclosure is not intended to be limited to the examples described herein and shown.

Analytical Techniques

XRPD patterns are obtained using a Bruker D8 Advance equipped with a Cu Kα radiation source (λ=1.54 Å), a 9-position sample holder and a LYNXEYE super speed detector. Samples are placed on zero-background, silicon plate holders for analysis. One skilled in the art would recognize that the ° 2θ values and the relative intensity values are generated by performing a peak search on the measured data and the d-spacing values are calculated by the instrument from the ° 2θ values using Bragg's equation. One skilled in the art would further recognize that the relative intensity for the measured peaks may vary as a result of sample preparation, orientation and instrument used, for example.

DSC data are collected using a TA Instruments Q10 DSC. Approximately, samples (2-8 mg) are placed in unsealed but covered hermetic alodined aluminum sample pans and scanned from about 30 to about 350° C. at a rate of about 10° C./min under a nitrogen purge of about 50 mL/min.

Some of the DSC runs are generated on a TA Instruments Q2000 equipped with an auto-sampler and RSC40. The sampling is conducted at a ramp rate of about 10° C./min from 20° C. to 320° C. using hermetic sealed aluminum sample pans. For mDSC (modulated DSC) data, samples are equilibrated at 5° C. with a ramp rate of 1.5° C. to 320° C., modulated ±0.50° C. every 60 seconds.

TGA measurements are recorded using TA Q500 instrument. The samples are weighed in aluminum pans. TGA investigations are performed at a heating rate of 10.0° C./min over a temperature range of from about 25 to about 300° C., with purging with nitrogen at a flow rate of 60 mL/min.

$^1$H-NMR data is collected using a Bruker Avance 300 MHz NMR equipped with TopSpin software. Samples are prepared by dissolving the compound in deuterated dimethylsulfoxide with 0.05% (v/v) tetramethylsilane (TMS). Spectra are collected at ambient temperature. The number of scans was $^1$H-NMR.

Crystalline morphology of samples are analyzed using an Olympus BX53 polarized light microscope equipped with a PAXcam 3 digital microscope camera.

Experimental

Examples 1-8 below provide embodiments of the preparation of dasatinib co-crystal and solvated forms.

Example 1

Preparation of Form I of Ethyl Formate Solvate of Dasatinib

About 120 mg of dasatinib is dispensed in about 1 mL of ethyl formate and stirred at temperatures of about 15° C. or about 45° C. for about 24 h. The slurries that are obtained at either of two temperatures are filtered, to yield Form I of ethyl formate solvate of dasatinib. The isolated Form I of ethyl formate solvate of dasatinib that is dried under vacuum at about 45° C. overnight (about 18-20 h) retains its form. Also, dried Form I of ethyl formate solvate of dasatinib that is subjected to high humidity conditions of about ≥95% relative humidity (RH) for overnight (about 18-20 h) retains its form.

FIG. 1 is the XRPD pattern for Form I of ethyl formate solvate of dasatinib that is made according to Example 1. Form I of ethyl formate solvate of dasatinib is characterized by its XRPD pattern peaks and their corresponding intensities that are listed in Table I below.

TABLE I

| Angle (2Θ) | Intensity |
|---|---|
| 6.0 | 52.3 |
| 12.1 | 32.1 |
| 15.1 | 100 |
| 15.9 | 5.7 |
| 17.6 | 6 |
| 18.0 | 46.4 |

TABLE I-continued

| Angle (2Θ) | Intensity |
|---|---|
| 18.4 | 14.4 |
| 18.9 | 23 |
| 21.6 | 21.4 |
| 23.1 | 23.8 |
| 24.3 | 27.5 |
| 24.8 | 53.1 |
| 26.0 | 15.5 |
| 26.3 | 8.3 |
| 32.7 | 6.5 |

The angle measurements are ±0.2° 2Θ. Key defining peaks for solid-state Form I of ethyl formate solvate of dasatinib include 6.0, 12.1, 15.1, 18.0, 23.8 and 24.8° 2Θ.

Figure 2:
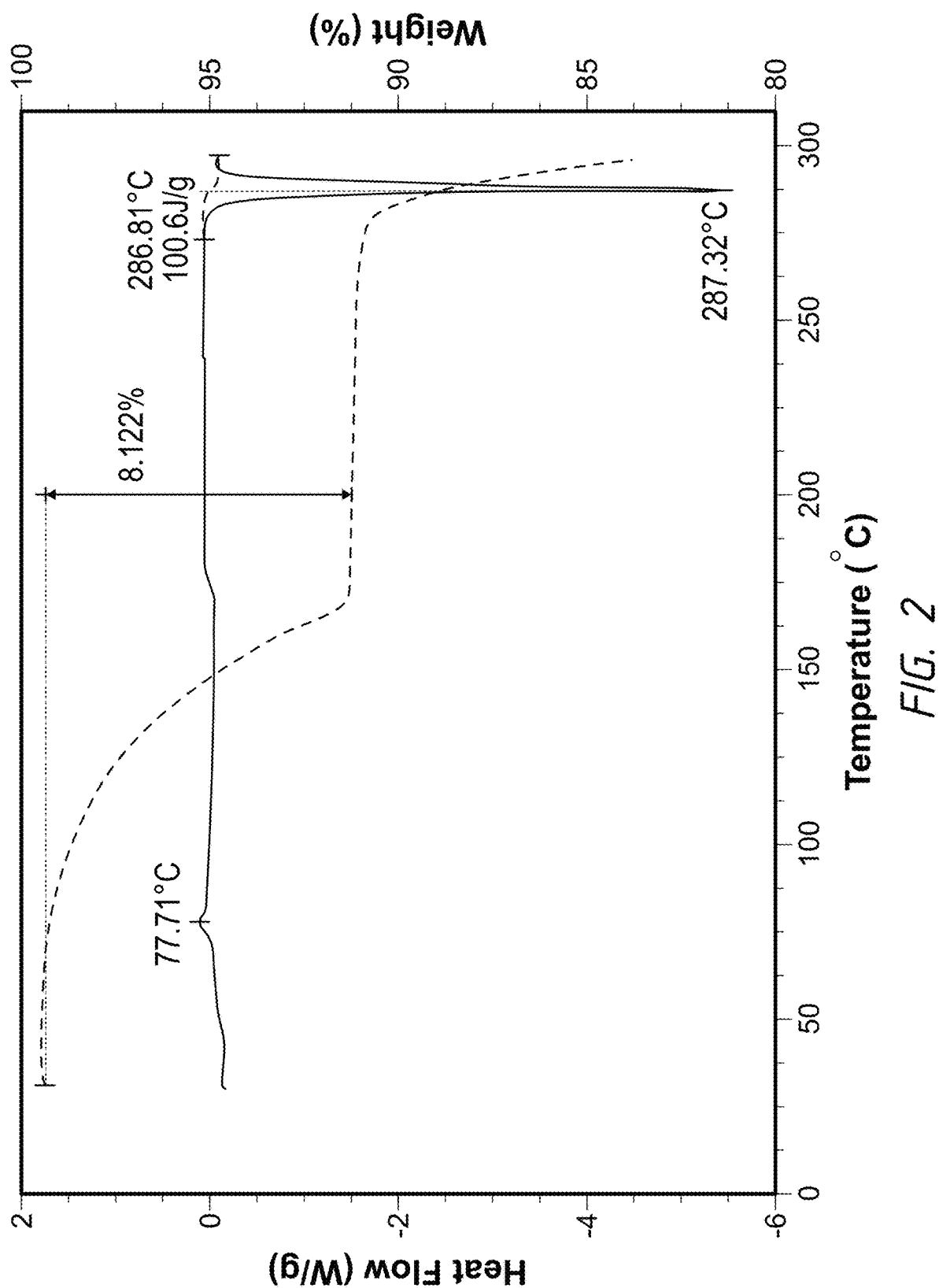
FIG. 2 are DSC and TGA plots of Form I of ethyl formate solvate of dasatinib.

The DSC and TGA plots (FIG. 2) show TGA weight loss of about 8.1% from about 70° C. through about 165° C., and DSC shows thermal event at 287.3° C. for Form I of ethyl formate solvate of dasatinib.

Figure 3:
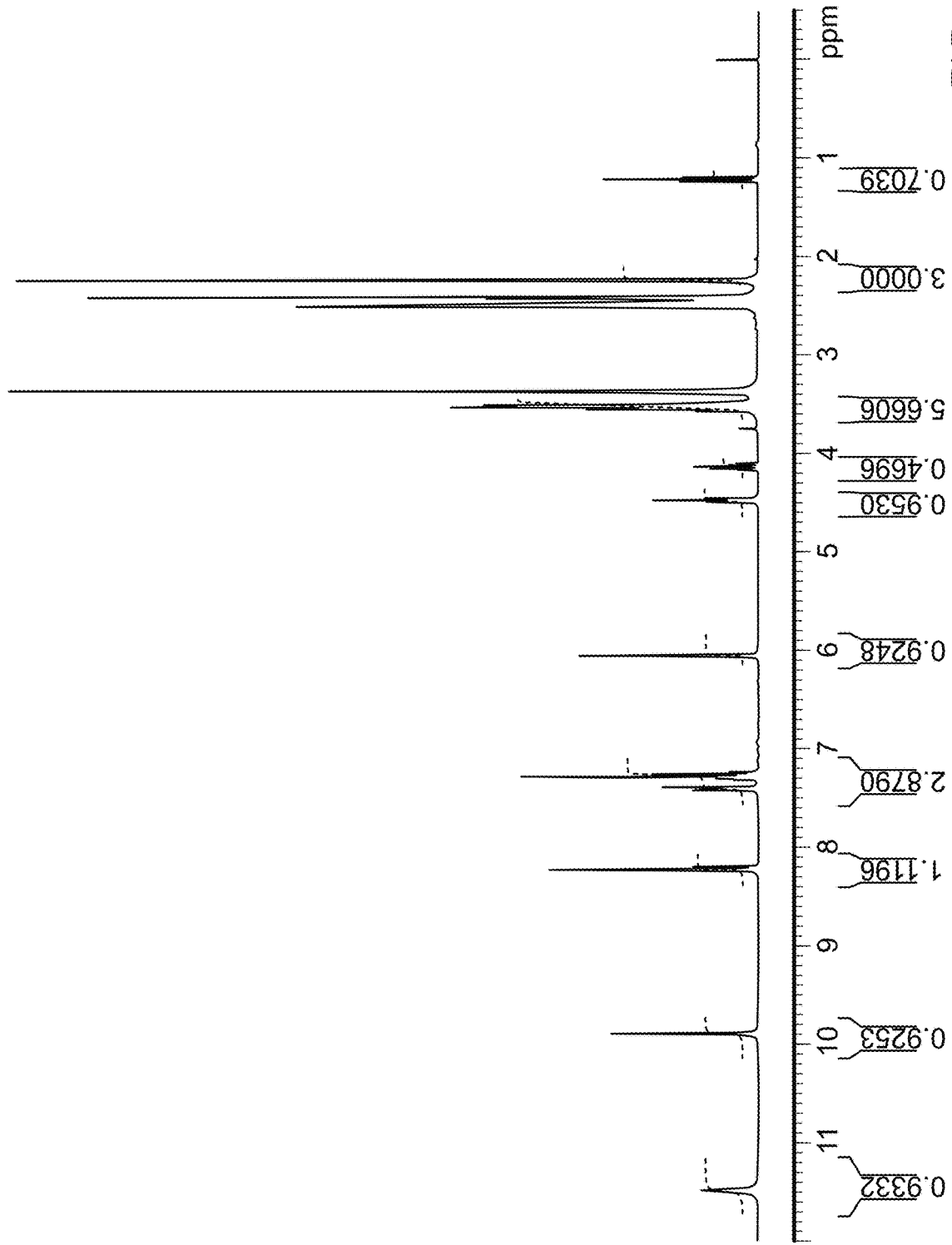
FIG. 3 is a $^1$H NMR spectra of Form I of ethyl formate solvate of dasatinib.

FIG. 3 is directed to the $^1$H NMR for the Form I of ethyl formate solvate of dasatinib.

Example 2

Preparation of Form I of Ethyl Formate Solvate of Dasatinib

About 1 g of dasatinib is dissolved in about 1.8 mL of NMP (N-methyl-2-pyrrolidone). About 7 mL of ethyl formate is added (about 1 mL at a time). White solids slowly crystallize out and the resultant slurry thickens. About 1 mL of additional ethyl formate is added and the slurry is stirred for about 2 hours. The slurry is filtered and the wet cake is washed with about 2 mL of ethyl formate to yield Form I of ethyl formate solvate of dasatinib.

Example 3

Preparation of Single Crystals of Form I of Ethyl Formate Solvate of Dasatinib

About 20 mg of Form I of ethyl formate solvate of dasatinib is added to 3 mL of ethyl formate at about 50° C. To this solution is added about 3 mL of methanol, and then the solution is stirred until a clear solution is obtained. The solution is evaporated to half the volume and capped for maturation at 40° C. to yield single crystals of Form I of ethyl formate solvate of dasatinib that are capable of being subjected to SCXRD.

Alternatively, about 100 mg of dasatinib is added to 0.5 mL of NMP at about 60° C. to dissolve. To the NMP solution, about 2 mL of ethyl formate is added and then cooled to 5° C. for about 18-20 h to yield Form I of ethyl formate solvate of dasatinib. Single crystals of Form I of ethyl formate solvate of dasatinib are isolated from the solution and subjected to SCXRD.

Figure 4:
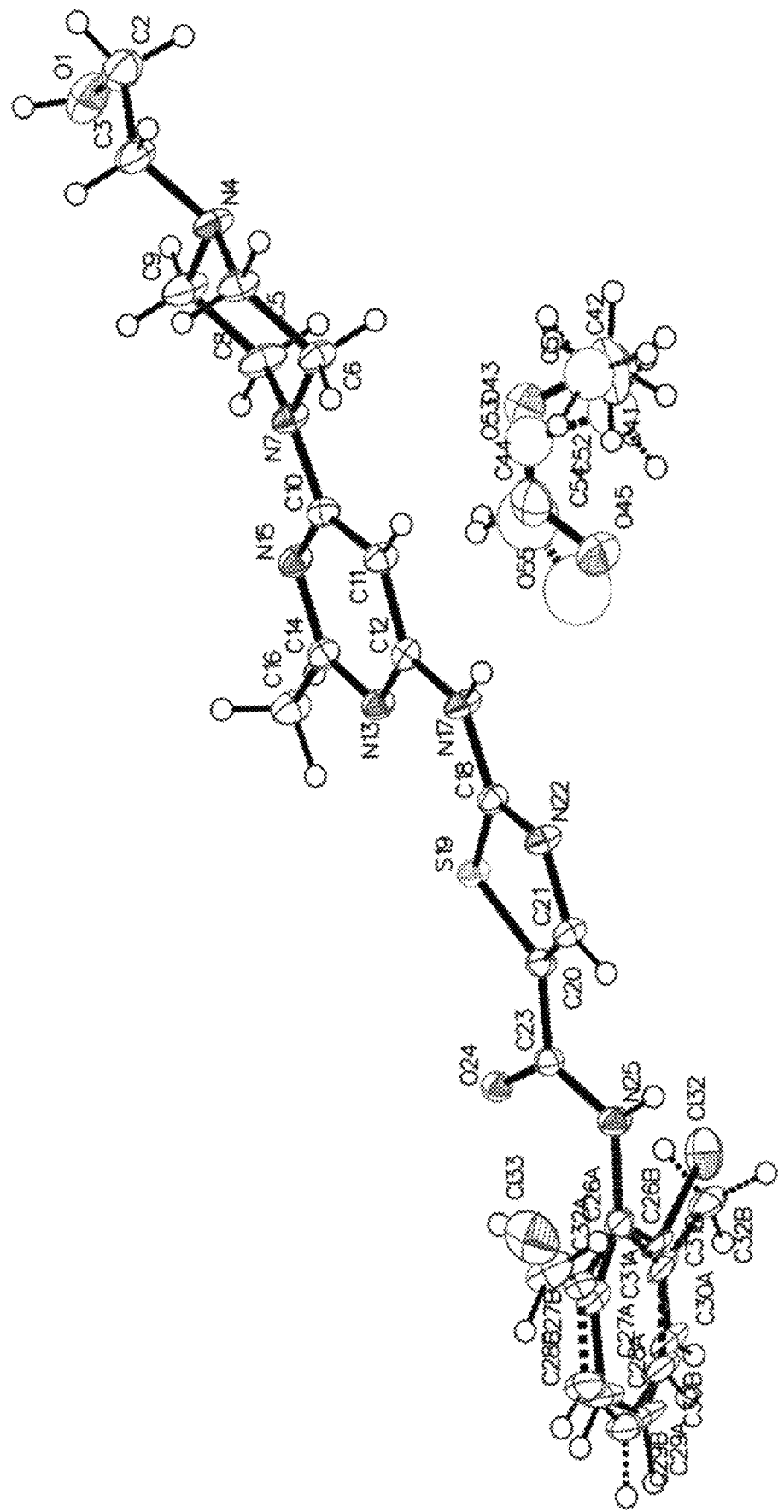
FIG. 4 is a three-dimensional structure of Form I of ethyl formate solvate of dasatinib that is discerned from SCXRD.
Figure 5:
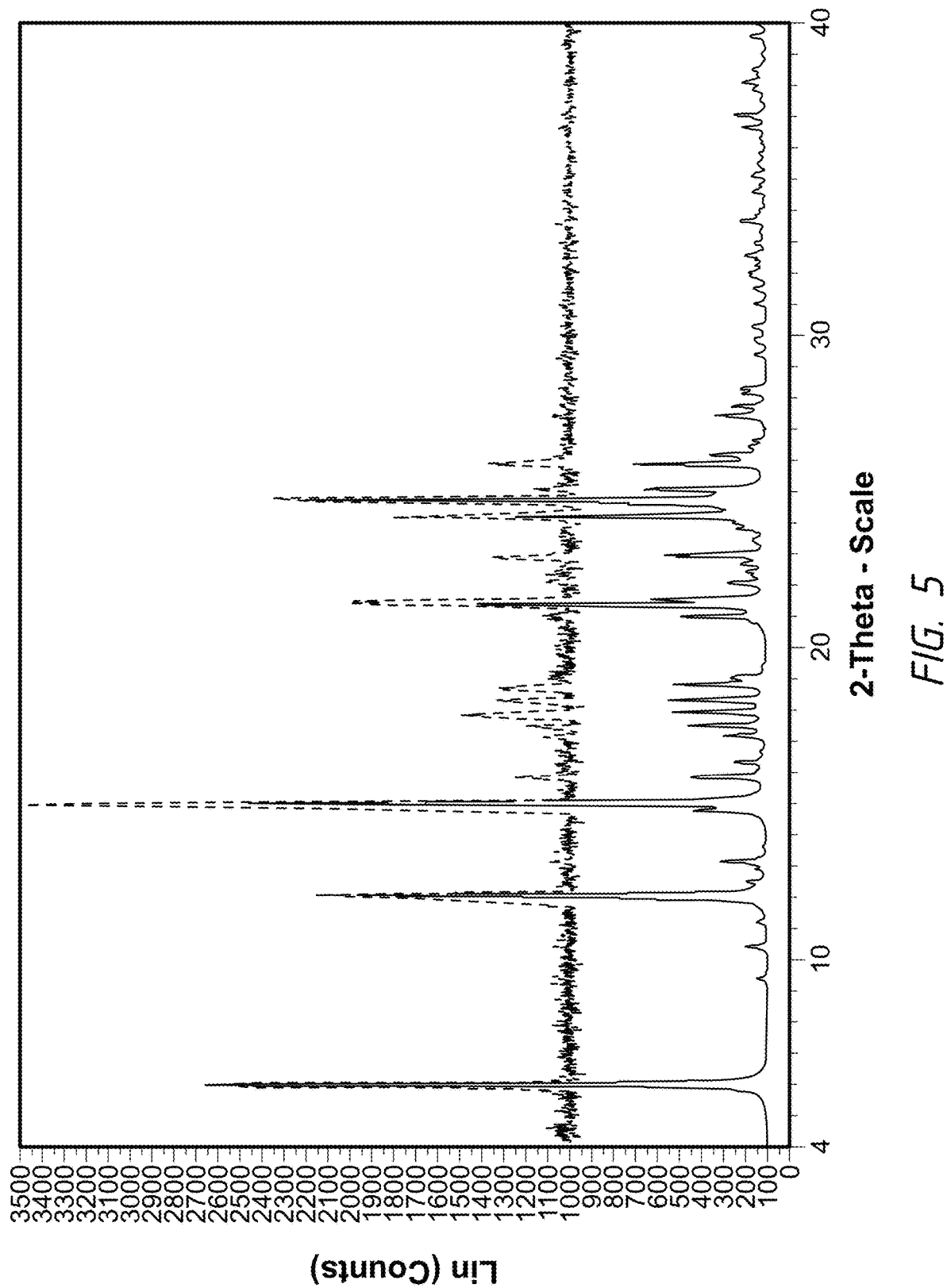
FIG. 5 shows the calculated XRPD pattern of Form I of ethyl formate solvate of dasatinib as determined by SCXRD (bottom) is in good agreement with the XRPD for Form I of ethyl formate solvate of dasatinib (top).

FIG. 4 shows the three-dimensional structure of Form I of ethyl formate solvate of dasatinib that is discerned from SCXRD. Single crystal parameters for Form I of ethyl formate solvate of dasatinib as determined by SCXRD are:

Crystal System: Orthorhombic, P2$_1$/c
a=14.8928 (5) Å
b=8.3299 (3) Å
c=22.18990 (6) Å
α=γ=β=90°
Cell Volume: 2731.9 Å$^3$ FIG. 5 shows that the calculated XRPD pattern of Form I of ethyl formate solvate of dasatinib as determined by SCXRD is in good agreement with the XRPD for Form I of ethyl formate solvate of dasatinib.

Example 4

Preparation of Form I Co-Crystal of Dasatinib and Butyl Paraben

About 50 mg of dasatinib and about 21 mg of butyl paraben are added to about 5 mL of methanol and heated to about 55° C. to obtain a clear solution. The clear solution is placed in the oven under vacuum at about 50° C. for solvent evaporation. The co-crystal is isolated the following day (about 18-20 h) and identified as Form I co-crystal of dasatinib and butyl paraben. Alternatively, the solvent in which the dasatinib is dissolved is a mixture of acetone (Ace) and water in a ACE:$H_2O$ of 7:3.

Figure 6:
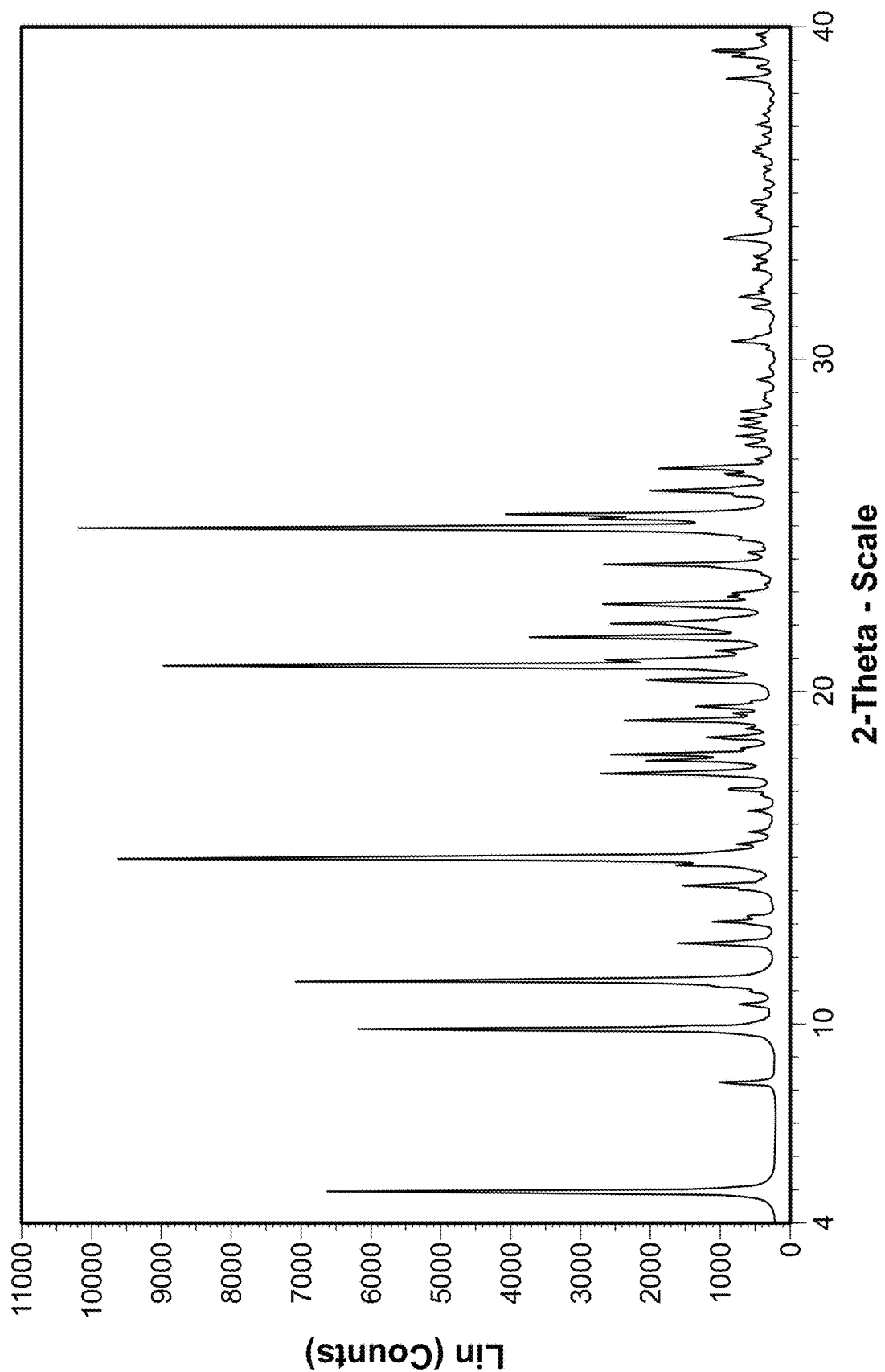
FIG. 6 is the calculated XRPD pattern of Form I co-crystal of dasatinib and butyl paraben.

FIG. 6 is the calculated XRPD pattern of Form I co-crystal of dasatinib and butyl paraben obtained by the instant method. Form I co-crystal of dasatinib and butyl paraben is characterized by its XRPD pattern peaks and their corresponding intensities that are listed in Table II below.

TABLE II

| Angle 2Θ<br>2-Theta ° | Intensity %<br>% |
|---|---|
| 4.9 | 70.6 |
| 9.8 | 68.5 |
| 11.3 | 77.8 |
| 12.4 | 15.1 |
| 14.1 | 14.5 |
| 14.9 | 100 |
| 17.5 | 29.3 |
| 18.1 | 28.2 |
| 19.2 | 25.8 |
| 20.8 | 96.3 |
| 21.6 | 41 |
| 22.1 | 27.5 |
| 22.6 | 28.8 |
| 23.8 | 27 |
| 24.9 | 60.3 |
| 25.4 | 45.1 |
| 26.0 | 19.8 |
| 26.7 | 20.3 |

The angle measurements are ±0.2° 2θ. Key defining peaks for solid-state Form I co-crystal of dasatinib and butyl paraben include 4.9, 9.8, 11.3, 14.9, 17.5, 20.8, 21.6, 22.6 and 25.4° 2θ.

The single crystal parameters for the Form I co-crystal of dasatinib and butyl paraben as determined by SCXRD are:

Space Group: Monoclinic, $P2_1/C$
a=18.630 (2) Å
b=8.725 (1) Å
c=22.331 (2) Å
α=γ=90°, β=104.575(8)°
Volume: 3512.9 Å$^3$
Z=4, Z'=1

Figure 7:
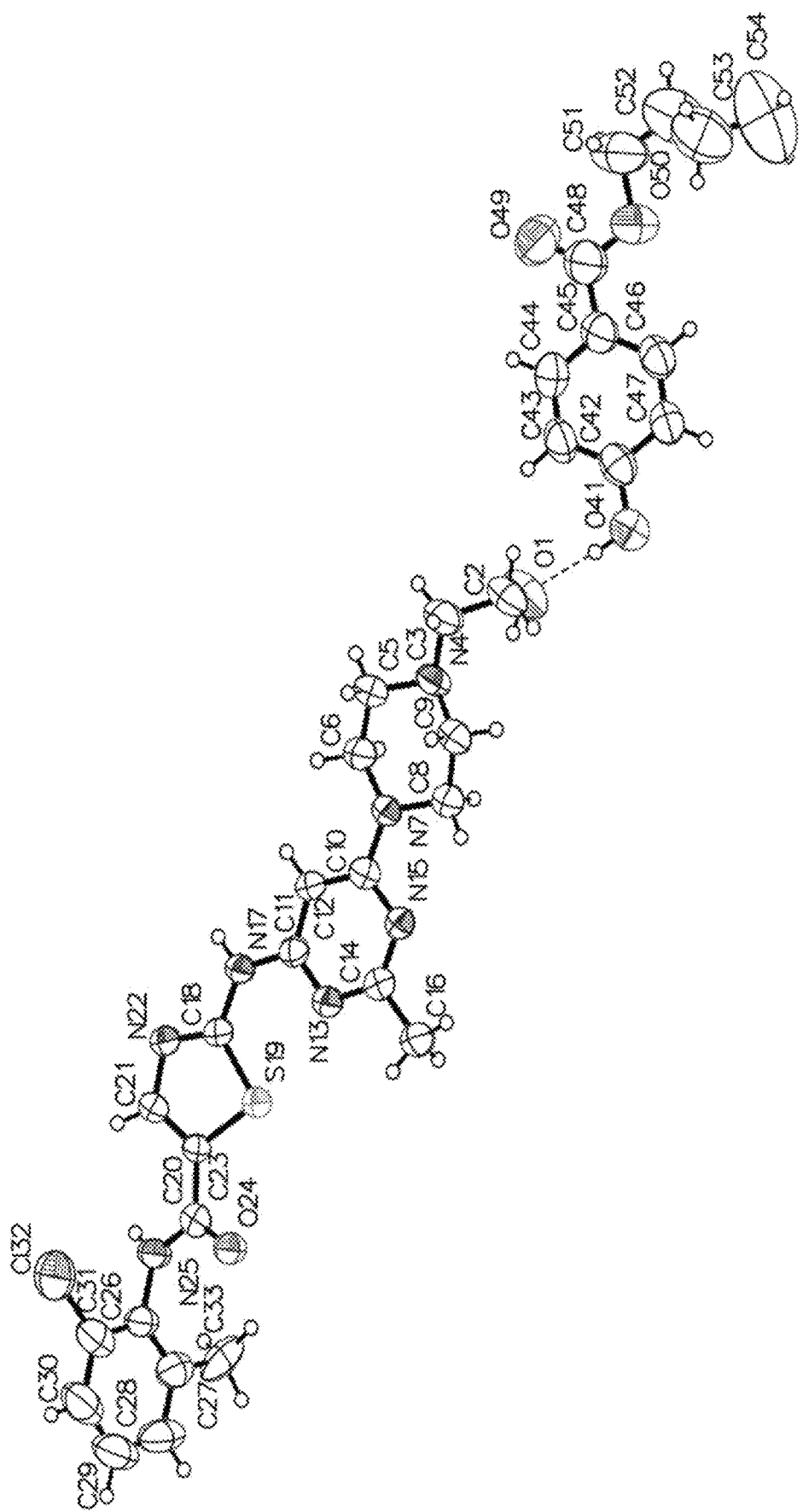
FIG. 7 shows the asymmetric unit of Form I co-crystal of dasatinib and butyl paraben.
Figure 8:
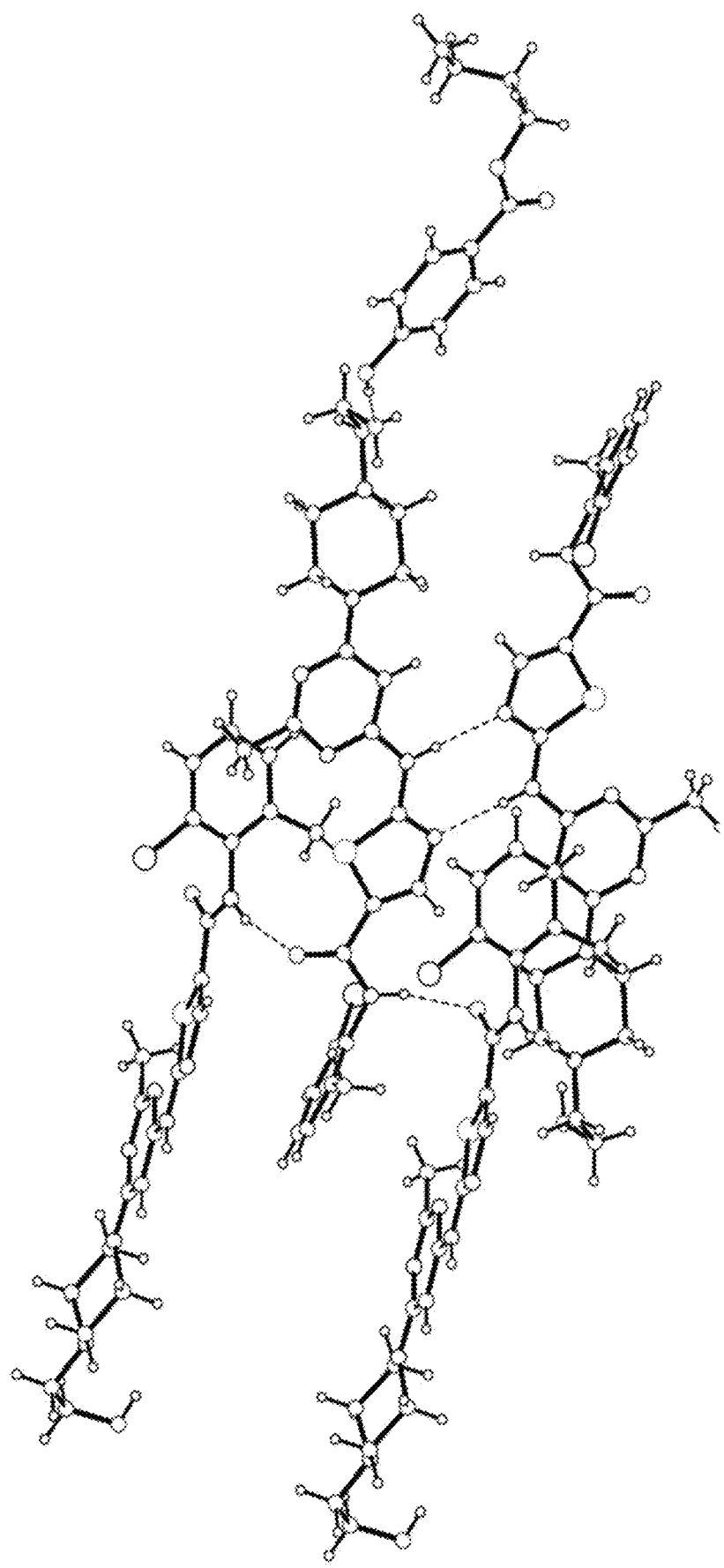
FIG. 8 shows the inter and intra molecular hydrogen bonding between dasatinib and butyl paraben molecules in Form I co-crystal of dasatinib and butyl paraben.

FIG. 7 shows the asymmetric unit of Form I co-crystal of dasatinib and butyl paraben. FIG. 8 shows the inter and intra molecular hydrogen bonding between dasatinib and butyl paraben molecules in Form I co-crystal of dasatinib and butyl paraben.

Example 5

Preparation of Form II Co-Crystal of Dasatinib and Ethyl Vanillin

About 50 mg of dasatinib and about 18 mg of ethyl vanillin are added to about 5 mL of methanol and heated to about 55° C. to obtain a clear solution. The clear solution is placed in the oven under vacuum at about 50° C. for solvent evaporation. The co-crystal is isolated the following day and identified as Form II co-crystal of dasatinib and ethyl vanillin.

Single crystals of Form II co-crystal of dasatinib and ethyl vanillin are obtained by the instant method, and the single crystal parameters for the Form II co-crystal of ethyl vanillin as determined by SCXRD are:

Space Group: Monoclinic, $P2_1/n$
a=18.452 (1) Å
b=9.441 (6) Å
c=19.377 (1) Å
α=γ=90°, β=108.78(1)°
Volume: 3195.71 Å$^3$
Z=4, Z'=1

Example 6

Preparation of Form II Co-Crystal of Dasatinib and Ethyl Vanillin Using Form I of Ethyl Formate Solvate of Dasatinib About 1.1 g of Form I of ethyl formate solvate of dasatinib and about 1.2 g of ethyl vanillin are dissolved in about 2.2 mL of NMP at about 60° C. Water (about 5 mL) is added slowly to the clear solution that initiates precipitation after about 30 sec. Then additional water (about 3 mL) is added, the heating is discontinued, and the solution is stirred at about room temperature overnight (18-20 h). The resultant precipitate is filtered, washed with about 5-6 mL of water and dried at about 45° C. overnight (18-20 h) to yield Form II co-crystal of dasatinib and ethyl vanillin.

Figure 9:
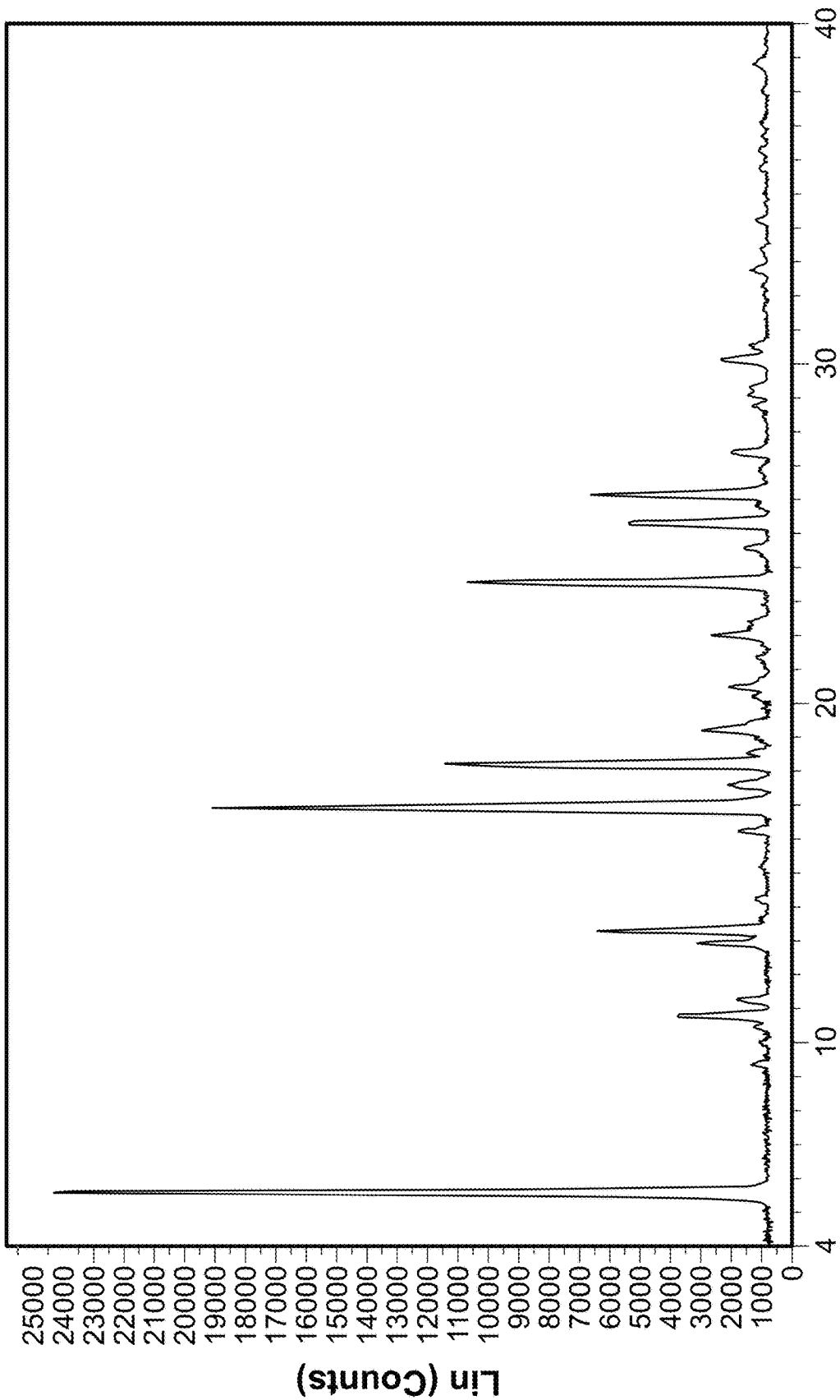
FIG. 9 is an XRPD pattern of Form II co-crystal of dasatinib and ethyl vanillin.

FIG. 9 is the XRPD pattern for Form II co-crystal of dasatinib and ethyl vanillin. Form II co-crystal of dasatinib and ethyl vanillin is characterized by its XRPD pattern peaks and their corresponding intensities that are listed in Table III below.

TABLE III

| Angle 2Θ<br>2-Theta ° | Intensity %<br>% |
|---|---|
| 5.7 | 100 |
| 9.0 | 12.5 |
| 10.9 | 44.1 |
| 13.5 | 43.5 |
| 16.4 | 13.8 |
| 17.1 | 38 |
| 18.4 | 45.2 |
| 19.4 | 30.3 |
| 23.7 | 97 |
| 25.4 | 20.7 |
| 26.3 | 58.5 |

The angle measurements are ±0.2° 2θ. Key defining peaks for solid-state Form II co-crystal of dasatinib and ethyl vanillin include 5.7, 10.9, 13.5, 17.1, 18.4, 19.4, 23.7 and 26.3° 2θ.

Figure 10:
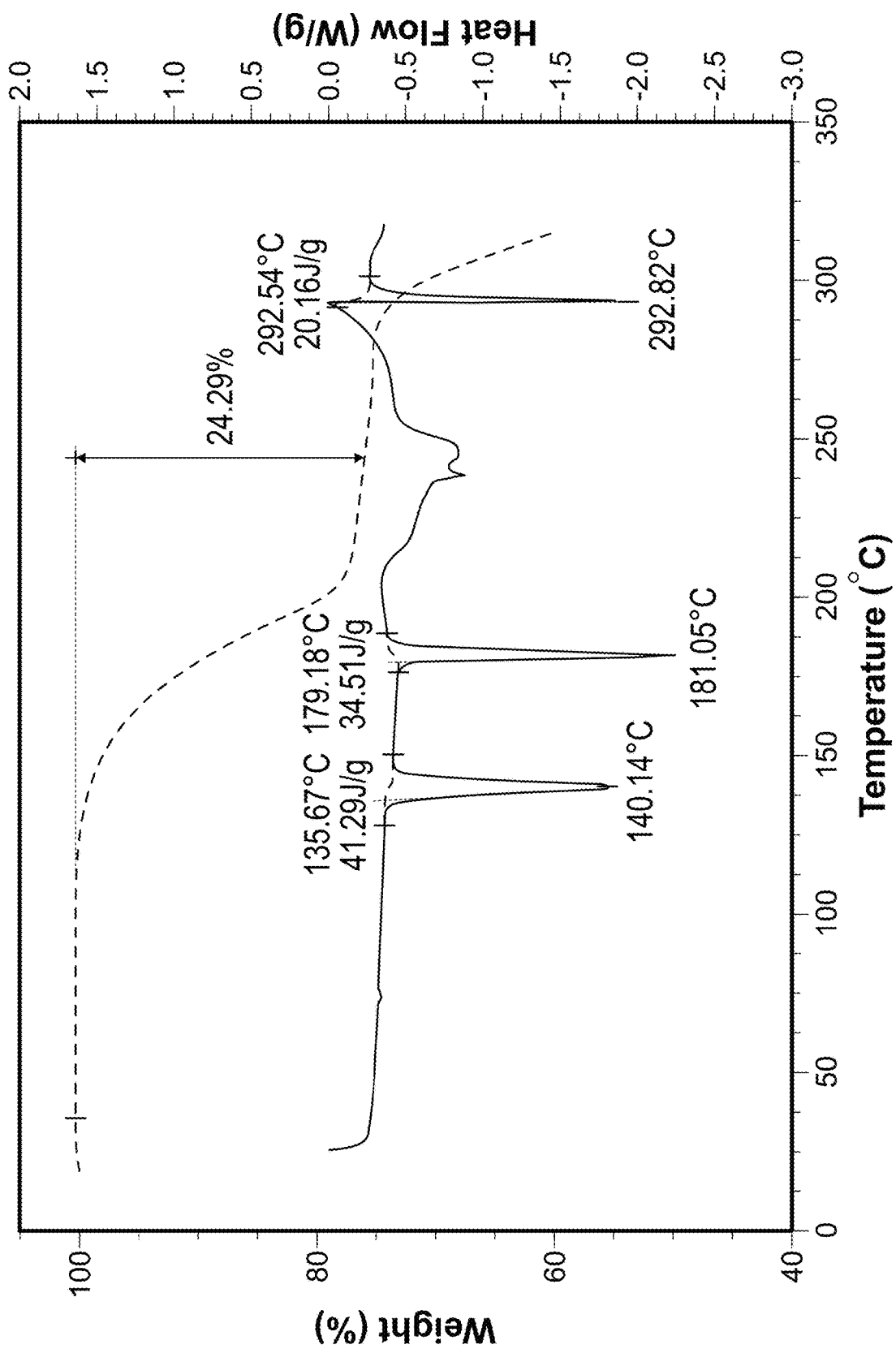
FIG. 10 are DSC and TGA plots of Form II co-crystal of dasatinib and ethyl vanillin.

The DSC and TGA plots (FIG. 10) for Form II co-crystal of dasatinib and ethyl vanillin show TGA weight loss of about 24.3% from about 120 through 250° C., and DSC shows thermal events at 140° C., 181° C., and 293° C. for Form II co-crystal of dasatinib and ethyl vanillin.

Figure 11:
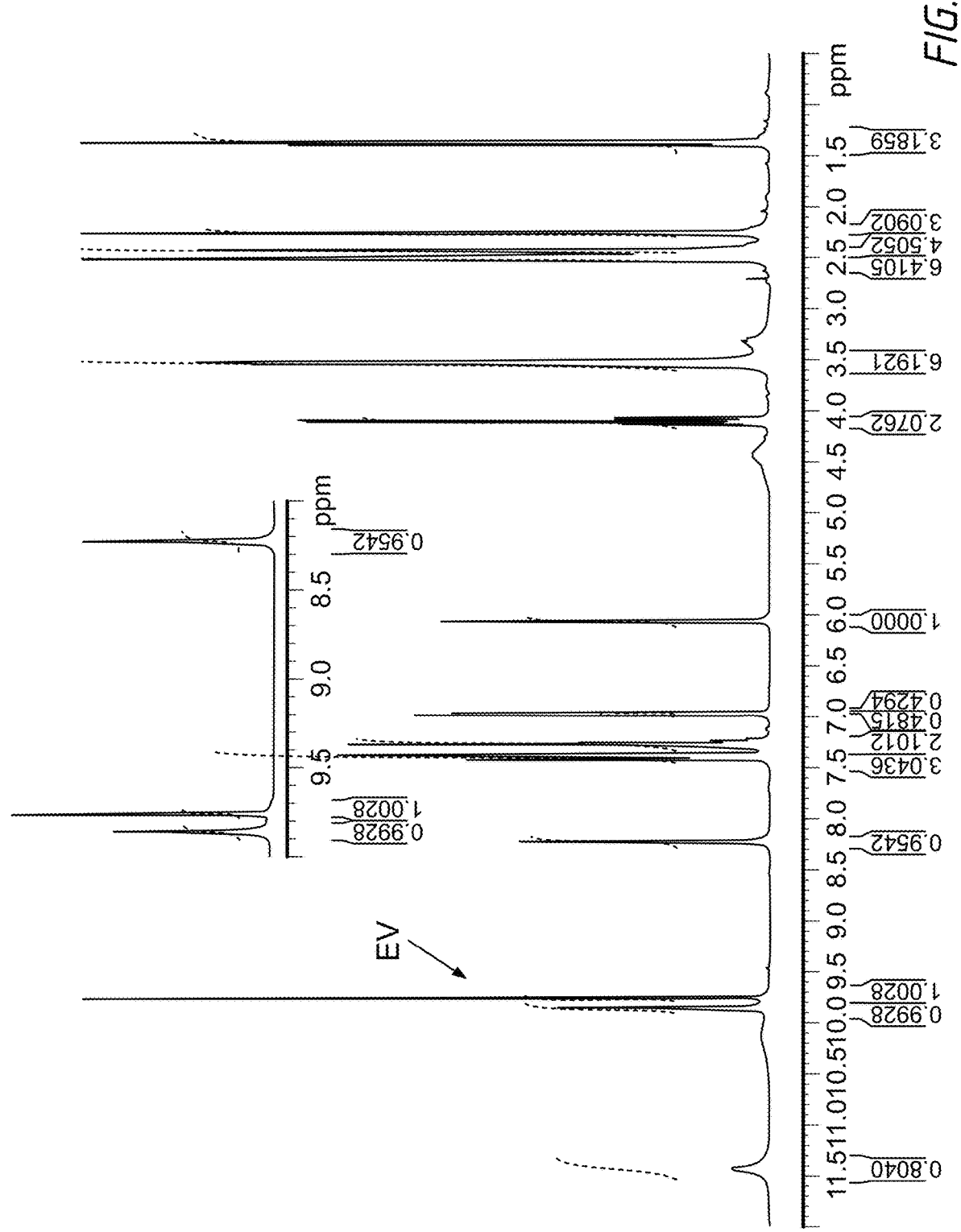
FIG. 11 is a $^1$H NMR spectra of Form II co-crystal of dasatinib and ethyl vanillin.

FIG. 11 is directed to the $^1$H NMR for the Form II co-crystal of dasatinib and ethyl vanillin.

Form II co-crystal of dasatinib and ethyl vanillin is stable (<1% moisture uptake) when exposed to 0-95% RH. Form II co-crystal of dasatinib and ethyl vanillin is also stable at 25° C./97% RH and 40° C./75% RH; and is stable up to 5 months under both conditions.

Figure 12:
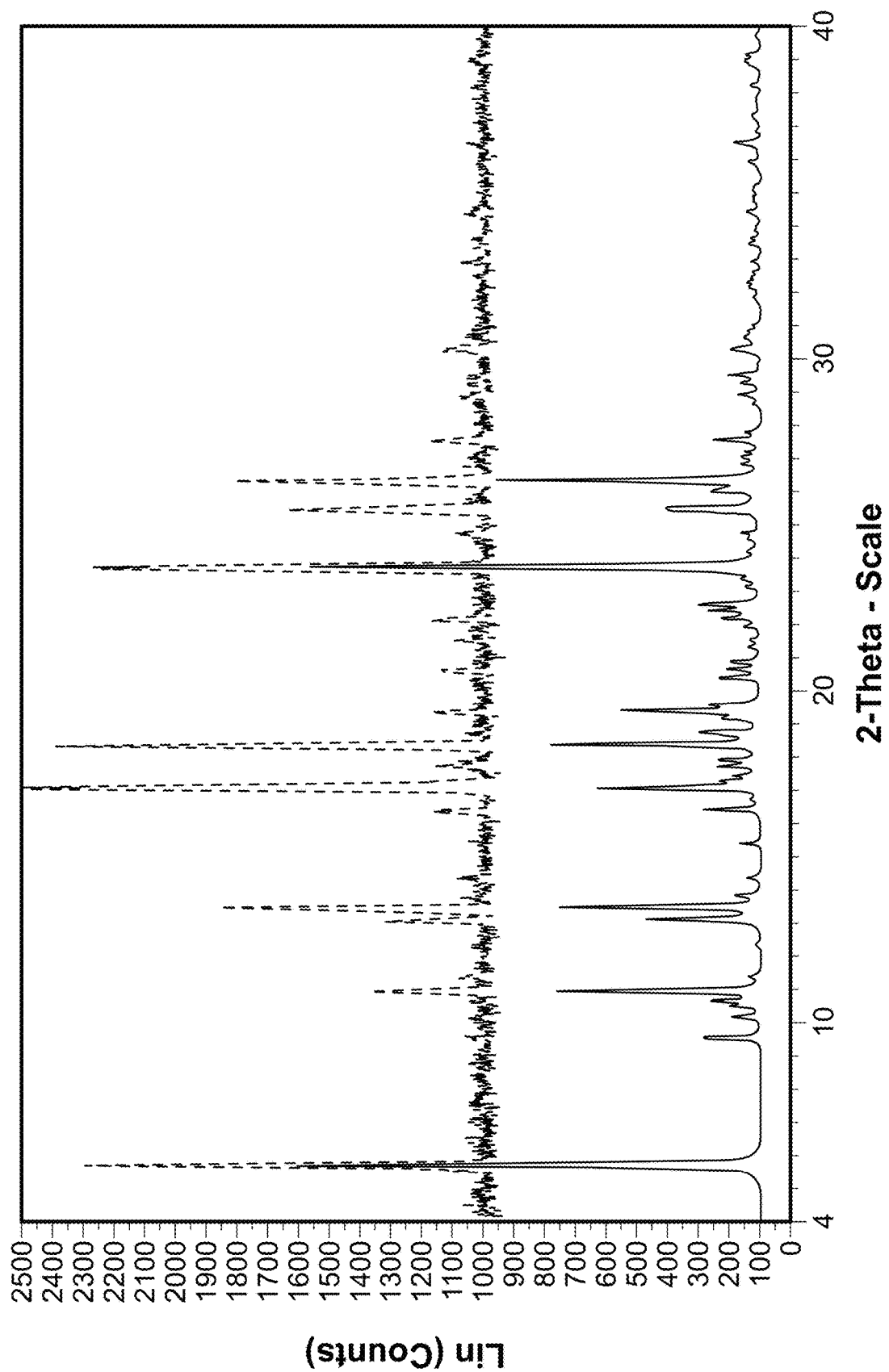
FIG. 12 shows that the calculated XRPD pattern of Form II co-crystal of dasatinib and ethyl vanillin as determined by SCXRD (bottom) is generally in good agreement with the XRPD for Form II co-crystal of dasatinib and ethyl vanillin (top).

FIG. 12 shows the calculated XRPD pattern of Form II co-crystal of dasatinib and ethyl vanillin as determined by SCXRD with the XRPD for isolated Form II co-crystal of dasatinib and ethyl vanillin.

Figure 13:
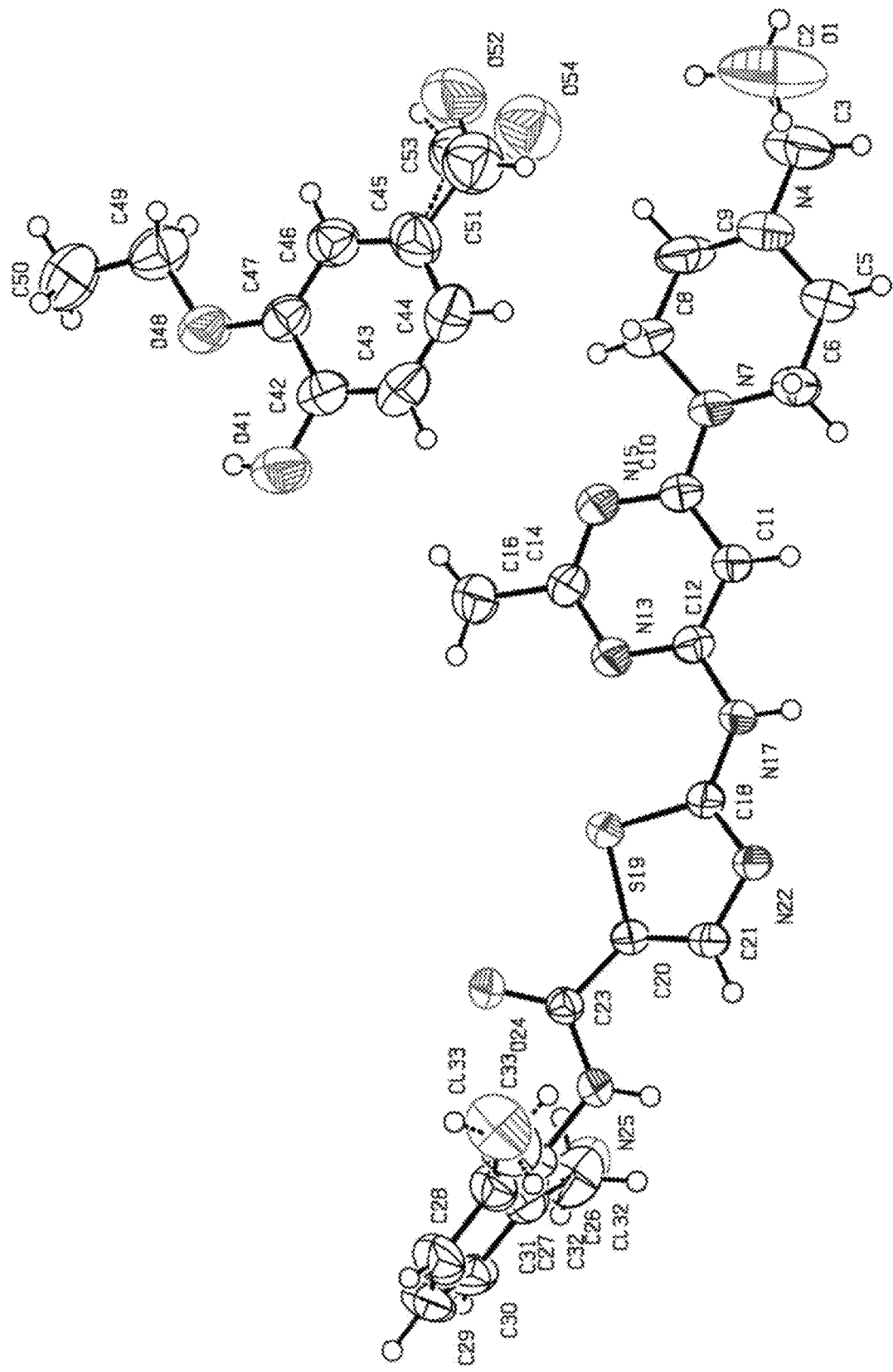
FIG. 13 shows the asymmetric unit of Form II co-crystal of dasatinib and ethyl vanillin. The asymmetric unit shows the 2-chloro-6-methylphen-1-yl moiety of the dasatinib is disordered over two positions (~1:1 ratio), and the aldehyde group of ethyl vanillin is disordered over two positions (0.73:0.27 ratio).

FIG. 13 shows the asymmetric unit of Form II co-crystal of dasatinib and ethyl vanillin.

Example 7

Preparation of Form II Co-Crystal of Dasatinib and Ethyl Vanillin Using Form I of Ethyl Formate Solvate of Dasatinib About 5.6 g of Form I of ethyl formate solvate of dasatinib and about 5.8 g of ethyl vanillin are dissolved in about 15 mL of NMP. Water (about 50 mL) is added slowly to the clear solution. After the addition of water, the heating is shut off and the reaction mixture is stirred at about room temperature overnight (18-20 h). The solid is filtered and the cake is washed with about 10-15 mL of water and the sample is dried at about 40° C. under vacuum over a weekend (18-20 h) to yield Form II co-crystal of dasatinib and ethyl vanillin.

Example 8

Preparation of Form III Co-Crystal of Dasatinib and Propyl Paraben

About 50 mg of dasatinib and about 20 mg of propyl paraben are added to about 5 mL of methanol and heated to about 55° C. to obtain a clear solution. The clear solution is placed in the oven under vacuum at about 50° C. for solvent evaporation. The co-crystal is isolated the following day and identified as Form III co-crystal of dasatinib and propyl paraben.

Figure 14:
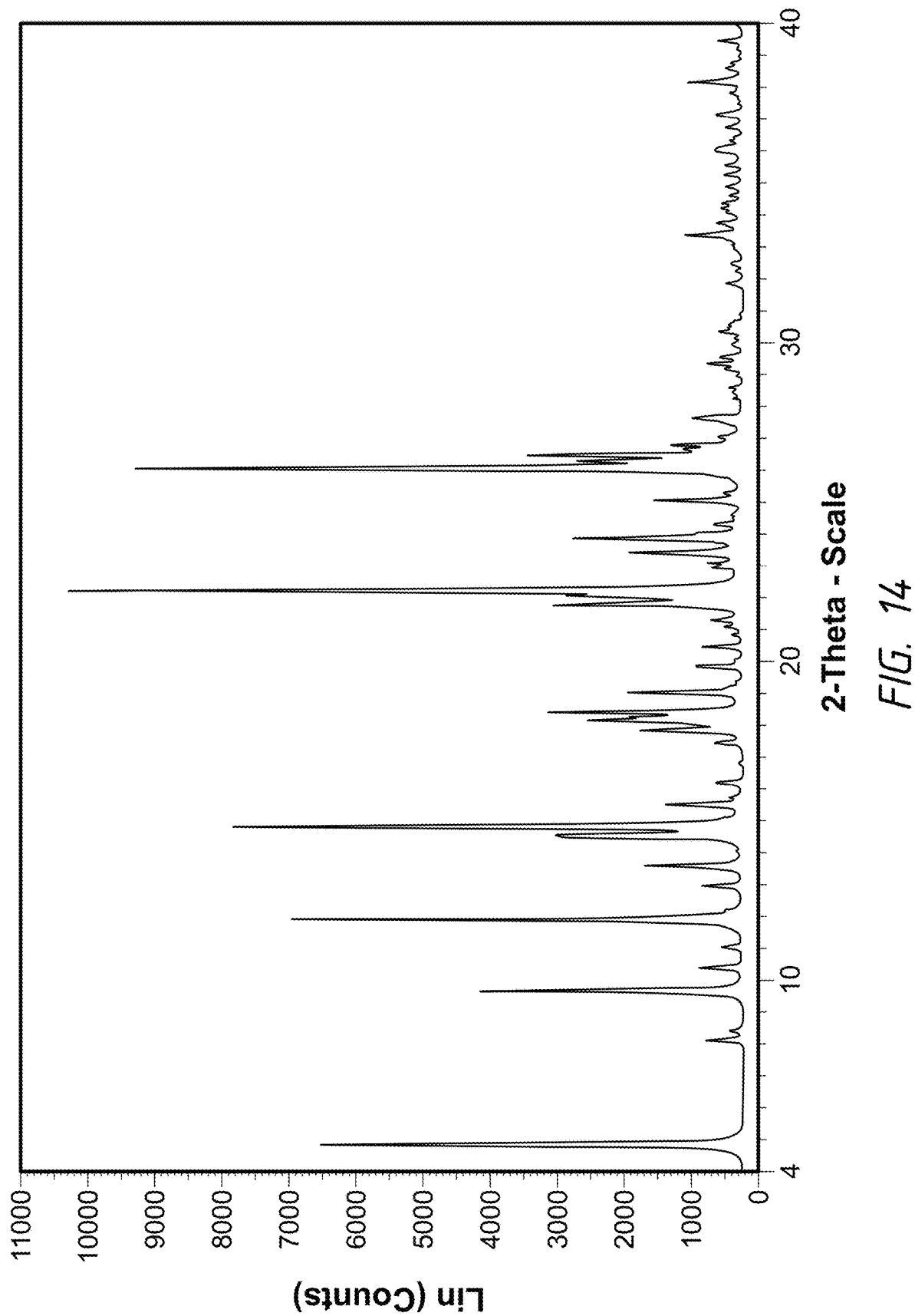
FIG. 14 is the calculated XRPD pattern of Form III co-crystal of dasatinib and propyl paraben.

FIG. 14 is the calculated XRPD pattern of Form III co-crystal of dasatinib and propyl paraben obtained by the instant method. Form III co-crystal of dasatinib and propyl paraben is characterized by its XRPD pattern peaks and their corresponding intensities that are listed in Table IV below.

TABLE IV

| Angle 2Θ 2-Theta ° | Intensity % % |
|---|---|
| 4.8 | 67.9 |
| 9.6 | 42.4 |
| 11.9 | 72.7 |
| 13.6 | 15.8 |
| 14.8 | 82.9 |
| 15.5 | 14.5 |

TABLE IV-continued

| Angle 2Θ 2-Theta ° | Intensity % % |
|---|---|
| 18.4 | 32.8 |
| 19.0 | 18.6 |
| 22.2 | 100 |
| 23.4 | 20.1 |
| 23.9 | 28.2 |
| 26.1 | 94.2 |

The angle measurements are ±0.2° 2θ. Key defining peaks for solid-state Form III co-crystal of dasatinib and propyl paraben include 4.8, 9.6, 11.9, 14.8, 18.4, 22.2, 23.9 and 26.1° 2θ.

The single crystal parameters for the Form III co-crystal of dasatinib and propyl paraben as determined by SCXRD are:

Space Group: Monoclinic, P2$_1$/n
a=18.859 (9) Å
b=8.131 (6) Å
c=22.473 (1) Å
α=γ=90°, β103.87 (1)°
Volume: 3345.51 Å$^3$
Z=4, Z'=1

Figure 15:
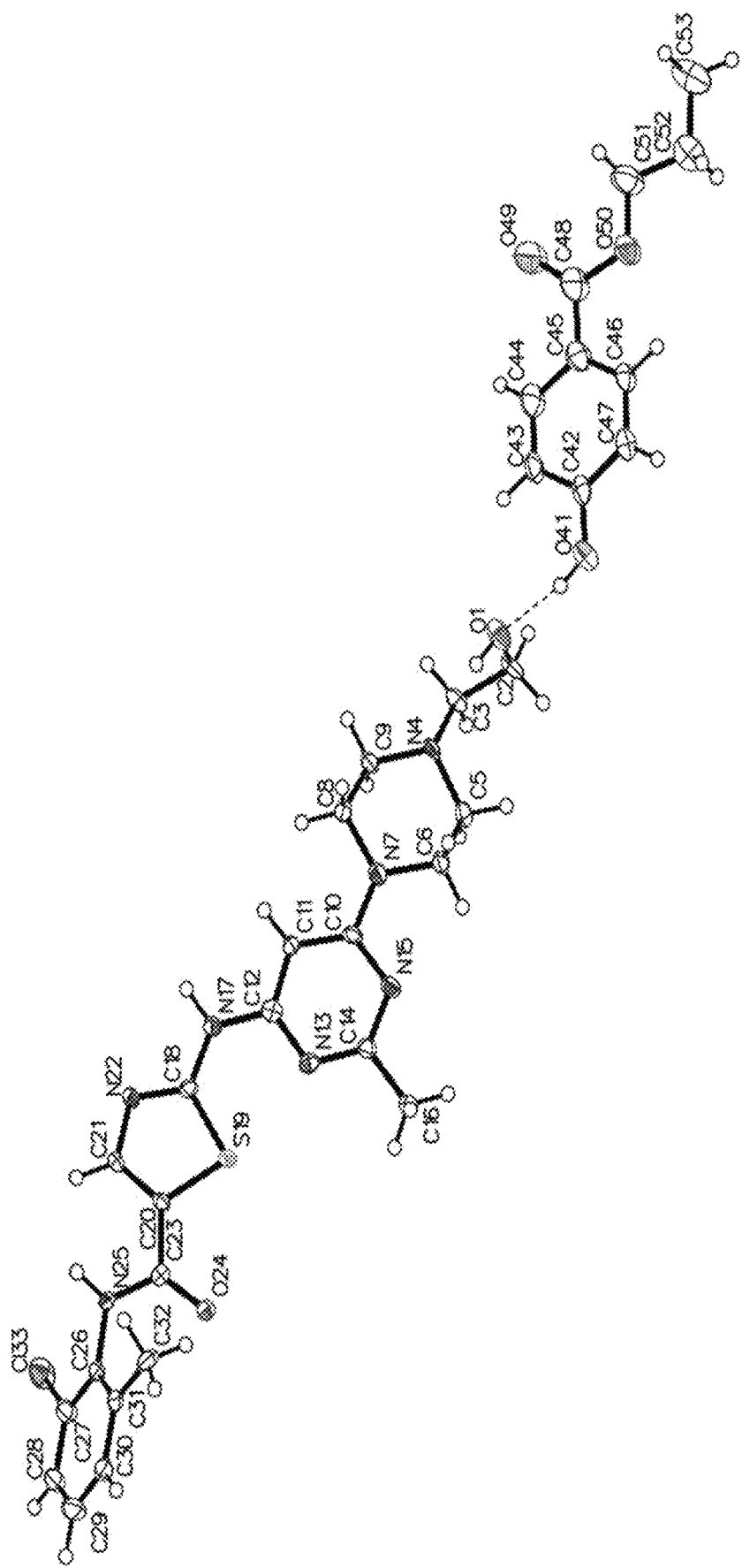
FIG. 15 shows the asymmetric unit of Form III co-crystal of dasatinib and propyl paraben.
Figure 16:
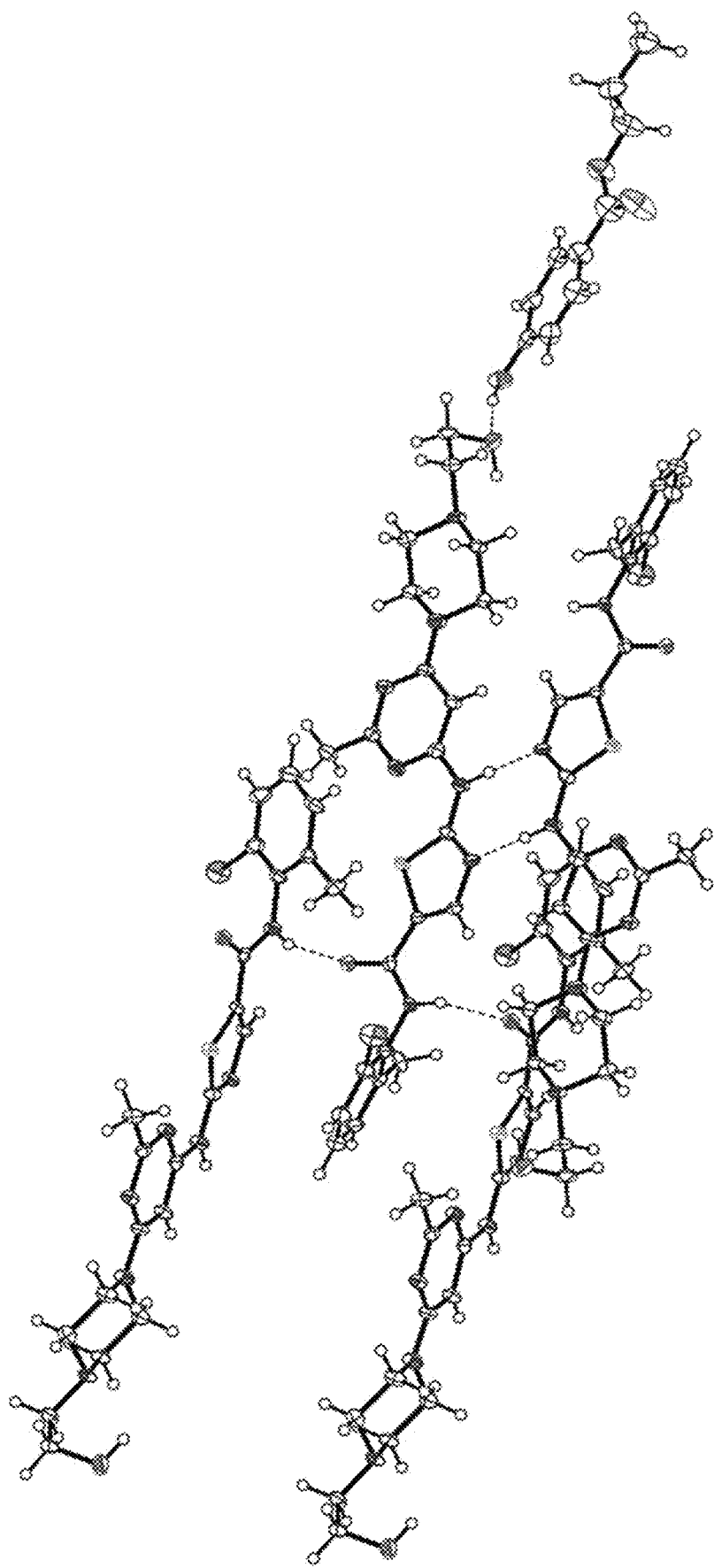
FIG. 16 shows the inter and intra molecular hydrogen bonding between dasatinib and propyl paraben molecules in Form III co-crystal of dasatinib and propyl paraben.

FIG. 15 shows the asymmetric unit of Form III co-crystal of dasatinib and propyl paraben. FIG. 16 shows the inter and intra molecular hydrogen bonding between dasatinib and propyl paraben molecules in Form III co-crystal of dasatinib and propyl paraben.

The above examples are presented to aid in the understanding of the disclosure and enable a person of ordinary skill in the art to make and use the various embodiments and are not intended and should not be construed to limit in any way the disclosure set forth in the claims which follow hereafter.

What is claimed is:

1. A dasatinib co-crystal comprising dasatinib and a second compound, wherein the second compound is ethyl vanillin, characterized by having at least 2 or more X-ray powder diffraction peaks selected from about 5.7, 10.9, 13.5, 17.1, 18.4, 19.4, 23.7 and 26.3° 2θ.

2. The dasatinib co-crystal according to claim 1, wherein a molar ratio of the dasatinib to the ethyl vanillin is about 1:1.

3. The dasatinib co-crystal according to claim 1, which is Form II co-crystal of dasatinib and ethyl vanillin.

4. The dasatinib co-crystal according to claim 3, characterized by one or more thermal events selected from about 140° C., about 181° C., and about 293° C., as measured by differential scanning calorimetry.

5. The dasatinib co-crystal of claim 3 which is monoclinic, P2$_1$/n.

6. The dasatinib co-crystal d of claim 3 which has single crystal parameters
a=18.452 (1) Å
b=9.441 (6) Å
c=19.377 (1) Å
α=γ=90°, η=108.78 (1°).

7. The dasatinib co-crystal of claim 3 which has a cell volume of about 3195.71 Å$^3$.

* * * * *